US00PP12749P2

(12) United States Plant Patent
Heims

(10) Patent No.: US PP12,749 P2
(45) Date of Patent: Jul. 2, 2002

(54) ***BETULA PENDULA* PLANT NAMED 'FILIGREE LACE'**

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/628,369

(22) Filed: Jul. 31, 2000

(51) Int. Cl.[7] ..... A01H 5/00
(52) U.S. Cl. ..... Plt./216
(58) Field of Search ..... Plt./216

(56) References Cited

U.S. PATENT DOCUMENTS

PP6,192 P * 5/1988 SaBell ..... Plt./216
PP10,963 P * 6/1999 Cheng et al. ..... Plt./216

* cited by examiner

*Primary Examiner*—Bruce R. Campell
*Assistant Examiner*—Wendy C Baker
(74) *Attorney, Agent, or Firm*—Klarquist Sparkman LLP

(57) ABSTRACT

A new and distinct *Betula pendula* plant characterized by a unique combination of extremely cut, thread-like foliage and dwarf, vigorous habit.

1 Drawing Sheet

The present invention relates to a new variety of *Betula pendula,* of the family Betulaceae, which originated as a discovery found under a mature *Betula pendula.*

The new variety has been reproduced only by asexual propagation (tissue culture). Each of the progeny exhibits identical characteristics to the original plant.

This plant is characterized by the following:

1. Extremely cut, thin leaf segments.
2. Dwarf, vigorous habit.

Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows *Betula pendula* 'Filigree Lace' in Canby, Oreg.

DETAILED PLANT DESCRIPTION

The following is a detailed description of the new *Betula pendula* variety based on observations of six year old specimens in Canby, Oreg. The color descriptions are all based on The Royal Horticultural Society Colour Chart.

Foliage:
- *Type.*—Simple. Deciduous.
- *Shape.*—Rhomboidal.
- *Length* (*leaf apex to point of petiole attachment*).—To 8 cm.
- *Width* (*segment apex to segment apex*).—May be open to 3 cm, but most are clasped together along its mid-vein to less than 1 cm.
- *Petiole length.*—2 cm.
- *Margins.*—Deeply cut to divided. Segments are lanceolate.

- *Apex.*—Very narrowly acute. Thread-like.
- *Base.*—Attenuate.
- *Segments width.*—2 mm tapering to 0.1 mm.
- *Leaf texture.*—Glabrate (above). Sandpaper-like (below). Puberulent (young plants). Architecturally superfine.
- *Petiole texture.*—Glabrous. Puberulent (young plants).
- *Stem texture.*—Warty due to peltate resin glands.
- *Leaf arrangement.*—Alternate.
- *Venation.*—Reticulate.

Size (6 years old plant grown in Canby, Oreg.):
- *Height.*—130 cm.
- *Width.*—90 cm.

Flower: No claim pertains to the flower. This plant has not flowered.

Fruit: Not seen.

Habit: Foliage and branches are weeping. Dwarf but vigorous.

Disease and pest: None observed on plants grown commercially in Canby, Oreg. However, leaf miner and bronze birch borer are serious pests of the species and its various cultivars.

Hardiness: USDA zones 2 to 6(7).

Color Characteristics

Foliage:
- *Upper surface.*—RHS 146B Yellow-Green Group.
- *Upper surface, veins.*—RHS 145C Yellow-Green Group.
- *Lower surface.*—RHS 146C Yellow-Green Group.

Stems: RHS 200C Brown Group but with RHS 152A Yellow-Green Group. RHS 148A Yellow-Green Group (young branchlets).

DESCRIPTION OF PARENT PLANTS

The instant plant was found under an unnamed, unpatented *Betula pendula. B. pendula,* as described in *A–Z Encyclopedia of Garden Plants* by the American Horticultural Society (1996), is a "Narrowly conical tree with pendent, warty branchlets and peeling white bark, which becomes marked with dark, rugged cracks at the base on older trees. Diamond-shaped, sharply toothed, mid-green leaves, to 2½ in (6 cm) long, turn yellow in autumn. Bears yellow-brown male catkins, to 2½ in (6 cm) long, in early spring . . . height 80' (25 m), width 30' (10 m)." The instant plant differs in having thread-like, deep green leaves, and is dwarf. The instant plant most resembles *B. pendula* 'Trost's Dwarf' (unpatented). *B. pendula* 'Trost's Dwarf', as described in *A–Z Encyclopedia of Garden Plants,* is "bushy and dwarf, with thread-like, deep green leaves; height 3–4' (1–1.2 m)." The instant plant differs from *B. pendula* 'Trost's Dwarf' in having leaves that are even more finely cut and grows much more vigorously. The instant plant also demonstrates a weeping habit as well as a preference for sun, this is not true for *B. pendula* 'Trost's Dwarf'.

I claim:

1. A new and distinct *Betula pendula* plant substantially as shown and described, characterized by a unique combination of extremely cut, thread-like foliage and dwarf, vigorous habit.

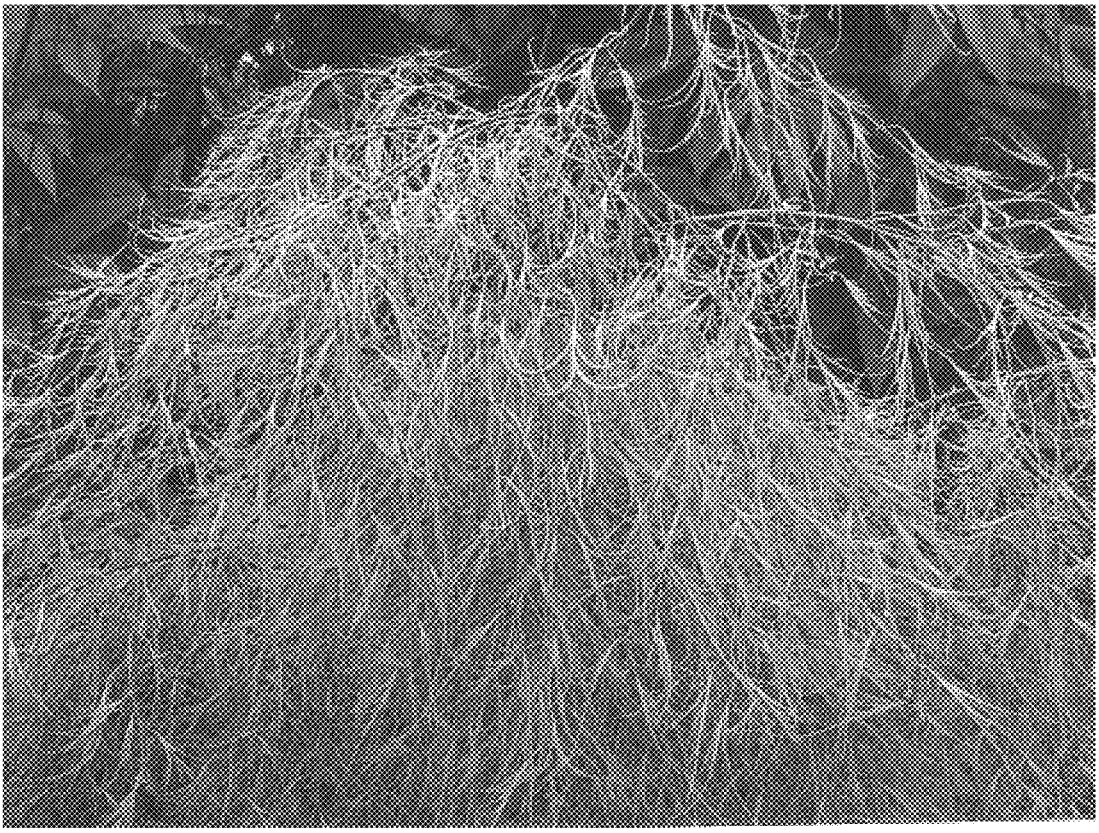

* * * * *